United States Patent [19]

Gutierrez et al.

[11] Patent Number: 4,474,674
[45] Date of Patent: Oct. 2, 1984

[54] MULTIFUNCTIONAL ADDITIVES FOR FUNCTIONAL FLUIDS AND LUBRICANTS

[75] Inventors: Antonio Gutierrez, Mercerville; Harold E. Deen, Cranford; Jack Ryer, East Brunswick; Stanley J. Brois, Westfield, all of N.J.

[73] Assignee: Exxon Research & Engineering Co., Florham Park, N.J.

[21] Appl. No.: 500,025

[22] Filed: Jun. 1, 1983

[51] Int. Cl.$^3$ .................. C10M 1/48; C10M 1/54; C10M 1/36
[52] U.S. Cl. ................... 252/47.5; 252/49.6; 252/49.7; 252/49.9; 260/462 R; 260/402.5; 260/429 R; 260/429.9; 260/439 R; 260/438.1
[58] Field of Search .................. 252/47.5, 49.6, 49.7, 252/49.9; 260/462 R, 429 R, 429.9, 402.5, 439 R

[56] References Cited

U.S. PATENT DOCUMENTS 4,198,304   4/1980   Inoue et al. ............ 252/47.5
4,394,277   7/1983   Small, Jr. ............... 252/49.6

Primary Examiner—Jacqueline V. Howard
Attorney, Agent, or Firm—J. J. Mahon

[57] ABSTRACT

There are disclosed novel multifunctional additives for power transmission shift fluids such as automatic transmission fluids which are diethanolamides or diisopropanolamides of alkyl thioglycolic acids or boron, phosphorous or metal reaction products thereof. These additives provide the properties of anti-oxidation, $H_2S$ suppression, corrosion inhibition and friction modification.

14 Claims, No Drawings

MULTIFUNCTIONAL ADDITIVES FOR FUNCTIONAL FLUIDS AND LUBRICANTS

This invention relates to novel additives for mineral lubricating oil compositions and functional fluids and compositions containing such additives.

More particularly this invention relates to certain dialkanolamides of alkyl thioglycolic acids and reaction products of such dialkanolamides with a boron compound, a lower alkyl phosphite or a complex-forming metal reactant. This invention further relates to lubricating oil compositions and functional fluids, such as power shift transmission fluids, containing these compounds as additives in amounts effective to provide one or more desirable properties to such compositions.

In accordance with the present invention there has been discovered a novel oil-soluble multifunctional additive for hydrocarbon mineral oil lubricant and functional fluid compositions, said additive being:

(a) a diethanolamide or disopropanolamide of a $C_{16}$–$C_{22}$ thioglycolic acid, the diethanolamide having the formula:

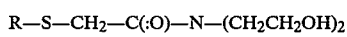

R—S—$CH_2$—C(:O)—N—($CH_2CH_2OH$)$_2$ and the disopropanolamide having the formula:

R—S—$CH_2$—C(:O)—N—(CH($CH_3$)$CH_2OH$)$_2$ and R is a $C_{16}$–$C_{22}$ n-alkyl or n-alkenyl, or (b) the reaction product of said diethanolamide or diisopropanolamide with a member of the group consisting of (i) a trialkyl phosphite or dialkyl hydrogen phosphite wherein the alkyl has 1 to 4 carbon atoms; (ii) a boron compound being a boron-containing oxide, acid or ester; and (iii) a complex forming metal compound, the metal being an alkali metal, alkaline earth metal or a transition metal.

The diethanolamide or diisopropanolamide are oil soluble compounds formed by reacting the alkyl thioglycolic acid with diethanolamine or diisopropanolamine in equimolar proportions at about 140°–160° C. Suitable thioglycolic acids may be generalized by the formula R—S—$CH_2$C(:O)OH where R is an n-alkyl or n-alkenyl of 16 to 22 carbon atoms, preferably about 18, with n-octadecyl thioglycolic acid being particularly preferred. It is essential that the alkyl or alkenyl be a straight chain.

The other category of novel additives of the present invention, which are reaction products with the alkanolamides, are formed by elimination of hydroxyl hydrogens of the diethanolamide or diisopropanolamide with the boron, phosphorous or metal atom bonding with the remaining oxygen atoms of the diethanolamide or diisopropanolamide moiety. In general the reaction between the alkanolamide of the thioglycolic acids and the phosphite, boron compound or metal compound may be carried out using equimolar proportions at temperatures of about 50° C. to 150° C., such as about 140° C., in an inert organic solvent such as xylene, toluene and the like. Solvent is removed and the product is isolated using conventional techniques.

Suitable phosphorous-containing reactants are the trialkyl phosphites or dialkyl hydrogen phosphites wherein the alkyl has about 1 to 4 carbon atoms such as trimethyl phosphite, triethyl phosphite, dibutyl phosphite and the like.

Reprsentative structures resulting from the reaction of a dialkyl hydrogen phosphite or trialkyl phosphite may be given by the formula:

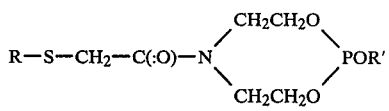

wherein POR' is the residue of the phosphite reactant, R' being hydrogen or $C_1$–$C_4$ alkyl. In this reaction, two moles of alcohol are eliminated in formation of the compound of the invention. R' is hydrogen when a dialkyl hydrogen phosphite is used. Phosphite reaction products are preferred when the additives of this invention are employed in tractor fluid formulations.

Borated additives represent a preferred embodiment since these additives have been found to be particularly effective multifunctional additives for power shift transmission fluids and offer improved oil solubility. Boron-containing compounds suitable for preparing the additive of the present invention include boron acids such as boric acid, a preferred material, alkyl, aryl and alkaryl boric acids having up to about 12 carbon atoms, boron oxide or boron oxide hydrate and mono-, di- or tri-substituted boric acid esters of $C_1$–$C_8$ alcohols or glycols.

A particularly preferred embodiment is a compound of the formula:

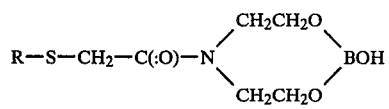

which is the reaction product of $H_3BO_3$ (boric acid) with the diethanolamide. R is preferably n-octadecyl.

The product formed by reacting $B(CH_3O)_3$, trimethyl borate with the thioglycolic acid diethanolamide may be represented by the formula:

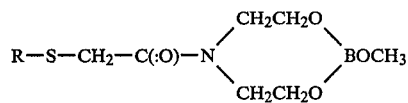

in which reaction two moles of $CH_3OH$ have been eliminated. Other alkyl borates would give similar structures.

The borated additives of the present invention may be prepared by reacting the diethanolamide or diisopropanolamide with the boron containing compound in a molar ratio of about 1:1 at elevated temperatures of about 100° to 250° C. in an inert hydrocarbon solvent, preferably a mineral oil solvent to facilitate the subsequent use of the products as additives for lubricants and power shift transmission fluids.

Suitable complex-forming metal reactants include the nitrates, nitrites, carboxylates, halides, carbonates, borates, sulfates, sulfites, phosphates and phosphites of alkali metals, alkaline earth metals and transition metals. Preferred metals are iron, cobalt, nickel, copper, zinc, molybdenum, calcium, magnesium and manganese which are preferably reacted as metal carboxylates of $C_1$–$C_4$ carboxylic acids, e.g. acetates, with the diethanolamide to form the useful additives of the present invention.

Reaction products of the metal compounds with the thioglycolic acid diethanolamide can be represented by the formula:

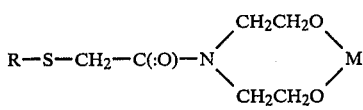

wherein M is a metal such as zinc, nickel or molybdenum. In this category of products, if the reactant were a metal acetate, the reaction would proceed by elimination of two moles of acetic acid.

A further embodiment of the present invention constitutes mineral oil based power transmission shift fluids such as automatic transmission fluids and other functional fluids containing the novel additives of the present invention in amounts effective to provide friction modification, anti-oxidant properties, copper and brass corrosion inhibition and/or H$_2$S suppression. This embodiment of the present invention is based on the discovery that these additives have multifunctional properties in such fluids when used at relatively low concentrations.

Accordingly, there have further been discovered in accordance with the present invention hydrocarbon mineral oil power transmission shift fluids comprising a major amount of a mineral oil of lubricating viscosity and an oil soluble multifunctional additive present in an amount effective to provide copper and brass corrosion inhibition, oxidation inhibition, friction modification and H$_2$S suppression, the additive being:

(a) a diethanolamide or diisopropanolamide of a C$_{16}$-C$_{22}$ thioglycolic acid, the diethanolamide having the formula:

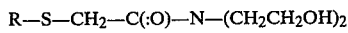

and the diisopropanolamide having the formula:

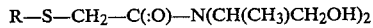

wherein R is C$_{16}$-C$_{22}$ n-alkyl or n-alkenyl, or (b) the reaction product of said diethanolamide or diisopropanolamide with a member of the group consisting of
  (i) a trialkyl or dialkyl hydrogen phosphite wherein the alkyl has 1-4 carbon atoms; and
  (ii) a boron compound being a boron-containing oxide, acid or ester; and
  (iii) a complex forming metal compound, the metal being an alkali metal, alkaline earth metal or a transition metal.

The compositions of the present invention may contain the additive generally within the range of about 0.01 to 1 wt% to provide the effective antioxidation, copper and brass corrosion inhibition, friction modification and H$_2$S suppression properties. Preferably, the power transmission shift fluids will contain about 0.1 to 0.75 wt% of the multifunctional additive of the present invention.

H$_2$S suppression refers to the ability of the additive of this invention to suppress the tendency of the power shift transmission fluid at elevated temperatures of about 130° F. and higher to form and liberate hydrogen sulfide. The formation of H$_2$S in such fluids may be due to the presence of sulfur in the fluid itself or the presence of sulfur in the other additives normally required in such as the antiwear, extreme pressure, corrosion and rust inhibitor additives.

In addition to use in automatic transmission fluids, the additive of the present invention will function as an oxidation inhibitor, corrosion inhibitor, friction modifier and H$_2$S suppressant in other power transmission shift fluids based on mineral oils such as hydraulic fluids, power brake and power steering fluids, heavy duty equipment fluids and the like.

The present invention is considered a substantial advance in the field of formulated power shift transmission fluids in that one additive will provide the properties normally associated with three or more additives, i.e. oxidation inhibition, corrosion inhibition friction modification and H$_2$S suppression, and these properties are achieved at a treatment or concentration level substantially lower than that required when the conventional systems are used which typically require two or three distinct additives.

Friction modifications is one of the most demanding properties to effectively provide in an automatic transmission fluid (ATF) and is considered the characteristic which distinguishes ATF compositions from other categories of lubricants. Very specific frictional properties related to transmission parts operation must be met in order to have an acceptable fluid. The additive of the present invention is highly advantageous in that it satisfies a significant friction modification test and simultaneously provides corrosion control and oxidation inhibition, thereby substantially reducing the complexity and cost of an effective automatic transmission fluid. The properties evaluated in ATF tests and specifications are generally applicable to other power shift transmission fluids.

Automatic transmission fluids containing the multifunctional additive of the present invention are the preferred embodiment. Improvements in oxidation stability of ATF has become recently of greater importance because of smaller sump capacities and increased load on a car's cooling system has increased transmission operating temperatures. Such ATF compositions contain a number of conventional additives in amounts sufficient to provide their normal attendant functions and are typically blended into the mineral oil base in the following ranges:

| Components | Concentration Range (Vol. %) |
|---|---|
| V. I. Improver | 1–15 |
| Corrosion Inhibitor | 0.01–1 |
| Oxidation Inhibitor | 0.01–1 |
| Dispersant | 0.5–10 |
| Pour Point Depresant | 0.01–1 |
| Demulsifier | 0.001–0.1 |
| Anti-Foaming Agents | 0.001–0.1 |
| Anti-Wear Agents | 0.001–1 |
| Seal Swellant | 0.1–5 |
| Friction Modifier | 0.01–1 |
| Mineral Oil Base | Balance |

Typical base oils for automatic transmission fluids and power transmission shift fluids generally include a wide variety of light hydrocarbon mineral oils, such as, naphthenic base, paraffin base and mixtures thereof, having a lubricity viscosity range of about 34 to 45 SUS (Saybolt Universal Seconds) and 38° C.

The invention is further illustrated by the following examples which are not to be considered as limitative of its scope. ATF compositions used in the examples below were formulated in accordance with the components (except corrosion inhibitor, oxidation inhibitor and friction modifier) and concentrations noted above and are referred to as Base Fluid.

EXAMPLE 1

Additive A was a borated diethanolamide of n-octadecyl thioglycolic acid having the formula:

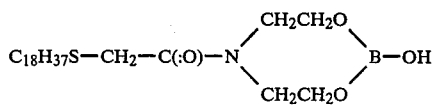

prepared by reacting equimolar quantities of $H_3BO_3$ with the diethanolamide.

Additive B was the diethanolamide of octadecyl thioglycolic acid having the formula:

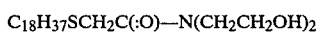

To a formulated automatic transmission fluid (Base Fluid) was added 0.4 wt% of Additive A. A separate fluid was prepared by addition of 0.3 wt% of additive B to the base fluid.

The fluids were evaluated in the LMOT (Laboratory Multiple Oxidation Test) and comparison was made with the Base Fluid. The same sample fluids were evaluated in Example 2.

In the LMOT test 50 ml. of the test fluid containing 2.0 g iron filings plus 0.5 g of a 1% solution of copper naphthenate oxidation catalyst is heated to 300° F. and 25 ml. of air per minute is bubbled through the sample. Daily samples are taken and blotter spots of the samples are observed for sludge. The number of days it took for visible sludge to appear is the measured rating of the antioxidation effect. A rating of 10–11 days or more is considered a "pass." The results are given below:

| LMOT RESULTS | |
|---|---|
| Base Fluid | 7 days |
| Base Fluid & Additive A | 19 days |
| Base Fluid & Additive B | 15 days |

EXAMPLE 2

Copper and brass corrosion tests were conducted which comprised immersing copper and brass specimens 3×½×1/6 inches weighed to 0.1 milligram in 40 cc. of the Example 1 ATF and maintaining the specimens in the fluid at 300° F. for 65 hours. Thereafter the specimens are washed in hexane, rubbed to remove any loose deposits and reweighed. Values of 30 mg copper and 15 mg brass, or less, are considered passing values for this test. These results, tabulated below satisfy current commercial specifications for automatic transmission fluids such as the General Motors Corp. specification for Dexron ® II Automatic Transmission Fluid.

| ATF | Cu loss, mg | Brass loss, mg |
|---|---|---|
| Base Fluid + Additive A | 11.0 | 0.6 |
| Base Fluid + Additive B | — | 0.6 |

EXAMPLE 3

ATF compositions containing the same additives evaluated in Example 1 and 2 were evaluated for friction modification in the Davison Friction Test utilizing the SAE No.2 friction machine and dynamic and static torque values were within the test specification of General Motors Corp. Dexron ® II specification for automatic transmission fluid (GM specification 6137-M, July, 1978)

EXAMPLE 4

The same ATF composition containing the additive evaluated in the foregoing examples was tested for $H_2S$ suppression. $H_2S$ suppression was measured by placing 50 ml samples of test fluid in a test tube which is heated to 300° F. in an aluminum block heater. The amount of $H_2S$ evaluation is measured in the test tube utilizing lead acetate strips manufactured for this purpose which record 0–200 units (arbitrary) of $H_2S$ evolved. The quantity of units evolved over a 3 or 4 hour period at 300° F. are recorded. Generally, conventional fully formulated ATF compositions will show $H_2S$ evolution after 3 hours in excess of 200 units in the absence of an $H_2S$ suppressant additive.

Base Fluid: 200 units after 1 hour
Base Fluid + Additive A: 140 units after 4 hours
Base Fluid + Additive B: 0 units after 4 hours

EXAMPLE 5

The same ATF Base Fluid with 0.4 wt% Additive A was evaluated in the Turbo Hydramatic Oxidation Test which is part of the Dexron ® II General Motors Corp. specification 6137-M for automatic transmission fluid and met all specification requirements with respect to total acid number, viscosity and increase in carbonyl group absorbance.

What is claimed is:

1. A novel compound being:
   (a) a diethanolamide or diisopropanolamide of a $C_{16}$–$C_{22}$ thioglycolic acid, the diethanolamide having the formula:

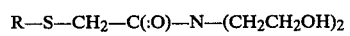

and the diisopropanolamide having the formula:

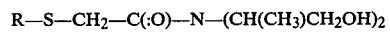

wherein R is a $C_{16}$–$C_{22}$ n-alkyl or n-alkenyl, or
   (b) the reaction product of said diethanolamide or diisopropanolamide with a member of the group consisting of (i) and trialkyl phosphite or dialkyl hydrogen phosphite wherein the alkyl has 1 to 4 carbon atoms; and (ii) a boron compound being a boron-containing oxide, acid or ester; and (iii) a complex forming metal compound, the metal being an alkali metal, alkaline earth metal or a transition metal.

2. The compound of claim 1 wherein R is n-octadecyl.

3. The compound of claim 1 wherein said diethanolamide or diisopropanolamide is reacted with a boron compound.

4. A compound of the formula:

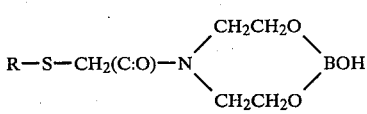

wherein R is n-octadecyl.

5. The compound of claim 1 wherein said diethanolamide or diisopropanolamide is reacted with a zinc, molybdenum or nickel carboxylate of a $C_1$–$C_4$ carboxylic acid.

6. The compound of claim 1 wherein the carboxylate is an acetate.

7. The compound of claim 1 wherein the diethanolamide or diisopropanolamide is reacted with a trialkyl or dialkyl hydrogen phosphite.

8. A hydrocarbon mineral oil power transmission shift fluid composition comprising a major amount of a mineral oil of lubricating viscosity and an oil soluble multifunctional additive present in an amount effective to provide copper and brass corrosion inhibition, oxidation inhibition, friction modification and $H_2S$ suppression, the additive being the reaction product of:

(a) a diethanolamide of a $C_{16}$–$C_{22}$ thioglycolic acid, the diethanolamide having the formula:

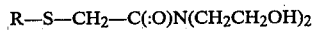

and the diisopropanolamide having the formula:

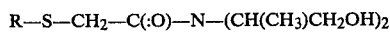

wherein R is $C_{16}$–$C_{22}$ n-alkyl or n-alkenyl or (b) the reaction product or said diethanolamide or diisopropanolamide with a member of the group consisting of (i) a trialkyl or dialkyl hydrogen phosphite wherein the alkyl has 1–4 carbon atoms; and (ii) a boron compound being a boron-containing oxide, acid or ester; and (iii) a complex forming metal compound, the metal being an alkali metal, alkaline earth metal or a transition metal.

9. The composition of claim 8 wherein there is present about 0.01 to 1.0 wt% of said additive.

10. The composition of claim 9 wherein said additive is the reaction product of said diethanolamide or diisopropanolamide with a boron compound.

11. The composition of claim 10 wherein said composition is an automatic transmission fluid formulated to contain conventional additives in amounts to provide their normal attendant functions.

12. The composition of claim 11 wherein said additive is a compound of the formula

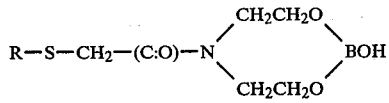

13. The composition of claim 12 wherein R is n-octadecyl.

14. The composition of claim 12 wherein there is present about 0.1 to 0.75 wt% of said additive.

* * * * *